US006746613B2

(12) United States Patent
Korenev

(10) Patent No.: US 6,746,613 B2
(45) Date of Patent: Jun. 8, 2004

(54) PULSED ELECTRIC FIELD SYSTEM FOR TREATMENT OF A FLUID MEDIUM

(75) Inventor: Sergey A. Korenev, Mundelein, IL (US)

(73) Assignee: Steris Inc., Temecula, CA (US)

( * ) Notice: Subject to any disclaimer, the term of this patent is extended or adjusted under 35 U.S.C. 154(b) by 0 days.

(21) Appl. No.: 10/287,123

(22) Filed: Nov. 4, 2002

(65) Prior Publication Data

US 2004/0084381 A1 May 6, 2004

(51) Int. Cl.$^7$ ................................................ C02F 1/461
(52) U.S. Cl. ........................ 210/748; 210/199; 210/243; 204/164; 205/701
(58) Field of Search ................................ 210/748, 764, 210/198.1, 199, 205, 243; 95/81; 422/22; 99/251; 204/164; 205/701, 742

(56) References Cited

U.S. PATENT DOCUMENTS

| | | | | |
|---|---|---|---|---|
| 4,457,221 A | * | 7/1984 | Geren | 99/451 |
| 5,766,447 A | * | 6/1998 | Creijghton | 205/742 |
| 5,776,529 A | | 7/1998 | Qin et al. | 423/231 |
| 6,030,538 A | * | 2/2000 | Held | 210/748 |
| 6,093,432 A | * | 7/2000 | Mittal et al. | 426/237 |
| 6,379,628 B2 | * | 4/2002 | de Jong et al. | 422/186.04 |
| 6,459,089 B1 | | 10/2002 | Masefield et al. | 250/453.11 |

OTHER PUBLICATIONS

U.S. patent application Ser. No. 10/090,573, filed Mar. 4, 2002, Korenev, entitled: Mobile Radiant Energy Sterilizer.

U.S. patent application Ser. No. 10/095,869, filed Mar. 12, 2002, Korenev et al., entitled: Method and Apparatus for Destroying Microbial Contimination of Mail.

Article entitled: "Design of Straus–R Accelerator," Gordeev et al., Russian Federal Nuclear Center–All–Russia Scientific Research Institute of Experimental Physics, Russia, BOΠ-POCbI ATOMHOй HAYKи и TEXHиKи, 2001, No. 3, pp. 56–58.

Article entitled "150 kV Magnetic Pulse Compressor," Mamaeve t al., Moscow Radiotechnical Institute of Russian Academy of Sciences, IEEE 1998, pp. 1311–1312.

Article entitled: "Pesudospark Discharge Physics," Frank et al., Pulsed Technologies Ltd., 2002, 2 pages.

Article entitled: "A New technology for Food Sterilization and Gaz/Liquid decontamination," Physique & industrie, 3 pages.

Article entitled: "Development of a Protein Fortified Fruit Beverage and its Quality when Processed with Pulsed Electric Field Treatment," Sharma et al., Journal of Food Quality 21, 1998, pp. 459–473.

Article entitled: "Nonthermal Inactivation of Saccharomyces cerevisiae in Apple Juice Using Pulsed Electric Fields," Qin et al., Lebebsm.–Wiss. u–Technol., 28, 1995, pp. 564–568.

(List continued on next page.)

Primary Examiner—Frank M. Lawrence
(74) Attorney, Agent, or Firm—Kusner & Jaffe

(57) ABSTRACT

A method and apparatus for treatment of a fluid medium to inactivate biocontamination using a pulsed electric field (PEF). A fluid medium is pumped through a treatment assembly to treat the fluid medium. A pulse generating system produces input pulses of high voltage that are supplied to the treatment assembly. A pulsed high intensity electric field associated with the input pulses is produced in a treatment assembly. As the fluid medium flows through the treatment assembly, it is exposed to the high intensity electric field, thereby treating the fluid medium. The pulse generating system includes a pulse compressor to reduce the rise time of the high voltage pulses supplied to the treatment assembly, and forming a pulsed electric field in space, without use of an electrode system.

33 Claims, 5 Drawing Sheets

OTHER PUBLICATIONS

Article entitled: *"Application of Pulsed Electric Fields for Inactivation of Bacteria and Enzymes,"* Qin et al., Journal of the Franklin Institute, vol. 332A, 1995, pp. 209–220.

Article entitled: *"Optimization of Solid–Phase Microextraction Analysis for Headdspace Flavor Compounds of Orange Juice,"* Jai et al., J. Agric. Food Chem., 46, 1998, pp. 2744–2747.

Article entitled: *"Inactivation of Listeria monocytogenes in Milk by Pulsed Electric Field,"* Renia et al., Journal of Food Protection, vol. 16, No. 9, 1998, pp. 1203–1206.

Article entitled: *"An Integrated PEF Pilot Plant for Continous Northermal Pasteurization of Fresh Orange Juice,"* Qiu et al., Transactions of the ASAE (American Society of Agricuktural Engineers,) vol. 41(4), pp. 1069–1074.

Article entitled: *"THE PureBright® PROCESS,"* PurePulse Technologies, Inc., San Diego, CA, 9 pages.

Article entitled: *"Investigation of Pulsed Light for Terminal Sterilization of WF1 Filled Blow/Fill/Seal Polyethylene Containers,"* Dunn et al., PurePulse Technologies, San Diego, CA, 6 pages.

Advertisement entitled: *"STERILE BY DESIGN™,"* Automatic Liquid Packaging Inc., Woodstock, IL, 1 page.

Advertisement entitled: "PureBright® *The Ideal Solution for Rapid On–Line Sterilization,*" PurePulse, 1 page.

Article entitled: *"Pulsed Electric Field Treatment Chamber Design for Liquid Food Pasterization Using a Finite Element Method,"* Qin et al., Transactions of the ASAE (American Society of Agricultural Engineers), vol. 38(2), 1995, pp. 557–565.

Article entitled: *"Food Pasterization Using High–Intensity Pulsed Electric Fields,"* Qin et al., Food Technology, Dec. 1995, pp. 55–60.

Article entitled: *"Inactivating Microorganisms Using a Pulsed Electric Field Continuous Treatment System,"* Qin et al., IEEE Transactions of Industry Applications, Jan./Feb. 1998, vol. 34, No. 1, pp. 43–50.

Article entitled: *"Northermal Pasteurization of Liquid Foods Using High–Intensity Pulsed Electric Fields,"* Qin et al., Critical Reviews in Food Science and Nutrition, 36(6), 1996, pp. 603–627.

Article entitled: *"The Effect of Pulsed Electrical Fields on Biological Cells,"* Schoenbach et al., Old Dominion University, IEEE, 1997, pp. 73–78.

Article entitled: *"Application of Pulsed Power Technology in Non–thermal Food Processing and System Optimization,"* Qiu et al., Ohio State University, IEEE, 1997, pp. 85–90.

\* cited by examiner

PULSED ELECTRIC FIELD SYSTEM FOR TREATMENT OF A FLUID MEDIUM

FIELD OF THE INVENTION

The present invention relates generally to the field of sterilization and pasteurization, and more particularly to a method and apparatus for treatment of a fluid medium to inactivate biocontamination using a pulsed electric field (PEF).

BACKGROUND OF THE INVENTION

High intensity pulsed electric field (PEF) processing is an effective means for treating a fluid medium, such as a liquid product (including, but not limited to, liquid foods and medicines), to inactivate biocontamination, such as microbes. PEF processing involves the application of a waveform comprised of high voltage pulses to a fluid medium flowing between a pair of electrodes. The pulses typically have a width in the range of 1 to 100 psec and a pulse frequency (i.e., pulse rate) in the range 1 to 10,000 pulses/sec. The high voltage pulses typically provide an electric field intensity in the range of 15 to 80 kV/cm. PEF processing is often recognized as superior to conventional thermal treatment of liquid foods, because it avoids or greatly reduces the detrimental changes of the sensory and physical properties of foods. At present, PEF processing is being used to improve food quality, such as extending the shelf-life of bread, milk, orange juice, liquid eggs, and apple juice, and to enhance the fermentation properties of brewers yeast.

A conventional PEF processing system includes a high voltage generator, a pulse generating circuit (e.g., an array of capacitors and inductors, and swithching devices) that produces high voltage pulses, and electrodes located in a treatment assembly. The electrodes receive the high voltage pulses, and produce an electric field. The liquid being treated flows between the electrodes, and thus receives exposure to the electric field.

There are several known methods for applying a PEF to a fluid medium. In this regard, the PEF may be applied in the form of exponentially decaying pulses, square wave pulses, bipolar pulses, instant-charge-reversal pulses, or oscillatory pulses. An exponential decay voltage wave is a unidirectional voltage that rises rapidly to a maximum value and decays slowly to zero. Square pulse waveforms are more lethal and more energy efficient than exponential decaying pulses. A square waveform can be obtained by using a pulse-forming network (PFN) consisting of an array of capacitors and inductors and switching devices. The instant-charge-reversal pulses are characterized by a positive voltage part ($+v_e$) followed by a negative voltage part ($-v_e$), with various widths and peak field strengths. There is no relaxation time between the positive and negative voltage parts. Bipolar pulses are pulses that reverse alternately, with a relaxation time between pulses. Research studies have indicated that oscillatory pulses seem to be the least efficient for microbial inactivation, because they prevent cells from being continuously exposed to a high intensity electric field for an extended period of time, thus preventing the cell membrane from irreversible breakdown over a large area.

The effectiveness of PEF processing is a function of several factors, including, but not limited to: electric field intensity, rise time of high voltage pulses for producing the pulsed electric field, number of pulses, pulse wave shape, treatment time (i.e., the product of the number of pulses applied and the duration of the pulses) processing temperature, characteristics of the target biocontamination, and the characteristics of the fluid medium (e.g., electrical conductivity of the medium, ionic strength of the medium, and viscosity and pH of the medium).

Several problems have been encountered in the prior art which have been observed to impair the effectiveness of PEF processing. For instance, prior art PEF processing systems generate high voltage pulses having long rise times. Furthermore, most prior art PEF processing systems have PEF treatment assemblies wherein the fluid medium flows past the electrodes in direct contact therewith. Consequently, over time, the electrodes are subject to corrosion due to contact with certain fluid mediums (e.g., corrosive liquids).

The present invention addresses these and other problems to provide an improved PEF processing system for treatment of fluid mediums.

SUMMARY OF THE INVENTION

In accordance with the present invention, there is provided an apparatus for exposing a fluid medium to a pulsed electric field, comprising (a) an energy storage circuit chargeable by a high voltage source; (b) switch means connected with the energy storage circuit, said switch means operable to form high voltage pulses; (c) a pulse compressing means for receiving the high voltage pulses and reducing a rise time for each of said high voltage pulses to produce a series of compressed high voltage pulses having a decreased rise front (i.e., shorter rise time); and (d) treatment assembly for receiving the fluid medium, said assembly comprising: (1) a dielectric flow tube providing a passageway for the fluid medium to travel through the treatment assembly, and (2) inductance means for receiving the series of compressed high voltage pulses, said inductance means producing a changing magnetic field in response to a change in voltage, which in turn induces an electric field, said electric field being pulsed in response to the compressed high voltage pulses, wherein said fluid medium passes through said pulsed electric field.

In accordance with another aspect of the present invention, there is provided a method for exposing a fluid medium to a pulsed electric field, comprising: (a) switching an energy storage element to form high voltage pulses; (b) compressing the high voltage pulses to reduce a rise time of each pulse, thereby producing compressed high voltage pulses; (c) exciting inductance means with the compressed high voltage pulses, wherein said compressed high voltage pulses produce a changing magnetic field, which in turn induces an electric field; (d) producing a series of electric field pulses in response to the high voltage pulses; and (e) exposing the fluid medium to the pulsed electric field.

In accordance with another aspect of the present invention, there is provided an apparatus for producing compressed pulses, comprising: (a) an outer conductor connected to ground; (b) an inner conductor connected with a switchable voltage source to receive one or more pulses of voltage having a first rise time; and (c) a magnetic material located between the inner and outer conductors.

In accordance with still another aspect of the present invention, there is provided an apparatus for exposing a fluid medium to a pulsed electric field, comprising: (a) a source of high voltage pulses; and (b) a treatment assembly including: (I) inductance means for receiving the high voltage pulses and inducing a pulsed electric field in response to the high voltage pulses, and (2) a passageway physically isolated from the inductance means, to pass the fluid medium through the pulsed electric field.

In accordance with yet another aspect of the present invention, there is provided a method for exposing a fluid medium to a pulsed electric field, comprising the steps of: (a) generating a series of high voltage pulses; (b) exciting inductance means with the series of high voltage pulses, wherein a pulsed electric field is induced in response to the high voltage pulses; (c) exposing the fluid medium to the pulsed electric field, wherein the fluid medium is physically isolated from the inductance means.

An advantage of the present invention is the provision of a PEF processing system that generates high intensity electric fields.

Another advantage of the present invention is the provision of a PEF processing system that generates electrical pulses having a short rise time.

Another advantage of the present invention is the provision of a PEF processing system that generates electrical pulses having an increased pulse rate.

Still another advantage of the present invention is the provision of a PEF processing system, including a treatment assembly, that physically isolates electrical components of the system from a fluid medium flowing therethrough.

Still another advantage of the present invention is the provision of a PEF processing system that reduces the required voltage level.

Yet another advantage of the present invention is the provision of a PEF processing system that provides an increase in throughput of fluids therethrough.

These and other advantages will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DETAILED DESCRIPTION OF A PREFERRED EMBODIMENT

Figure 1:
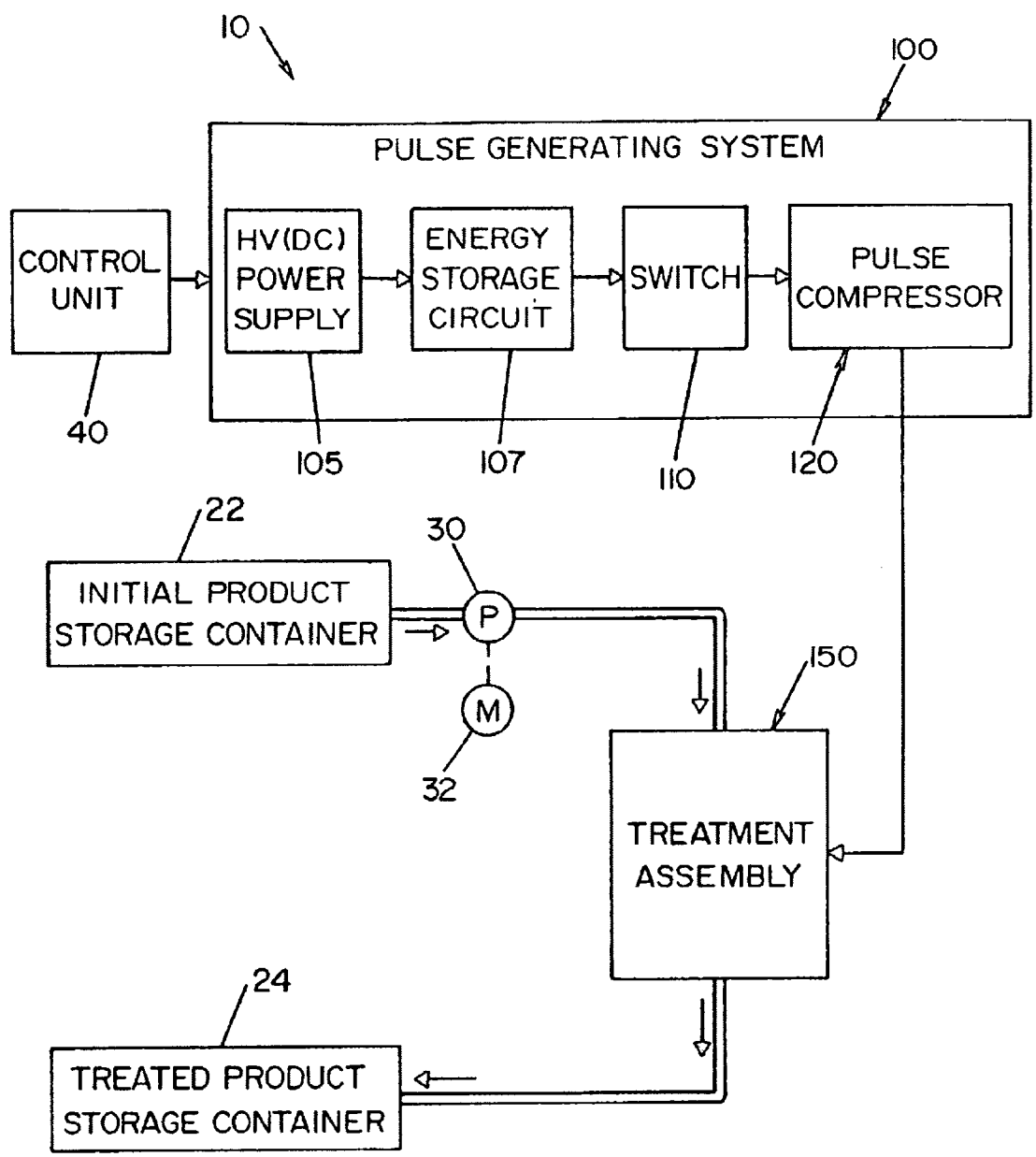
FIG. 1 is a block diagram illustrating a PEF processing system, according to a preferred embodiment of the present invention.

Referring now to the drawings wherein the showings are for the purposes of illustrating a preferred embodiment of the invention only and not for purposes of limiting the same, FIG. 1 shows a block diagram of a PEF processing system 10 for treating fluid mediums, illustrating a preferred embodiment of the present invention. PEF processing system 10 is generally comprised of an initial product storage container 22, a treated product storage container 24, a pump 30 and associated motor 32, a control unit 40, a pulse generating system 100, and a treatment assembly 150 having a flow tube 152 made of a dielectric material. It should be understood that the term "fluid medium," as used herein, refers to a flowable medium, including but not limited to, liquids (e.g., a liquid food product or a liquid medicine product), small solid particles, and gases.

Basically, a fluid medium stored in storage container 22 is pumped out of storage container 22, through treatment assembly 150, and into storage container 24. Pulse generating system 100 produces pulses of high voltage that are supplied to treatment assembly 150. A high intensity electric field associated with the pulses is produced in treatment assembly 150. The fluid medium flowing through treatment assembly 150 is exposed to this high intensity electric field, thereby treating the fluid medium.

Control unit 40 controls operation of switch 110 of pulse generating system 100, as will be explained in detail below. In a preferred embodiment, control unit 40 takes the form of a conventional personal computer (PC). 100321 Pulse generating system 100 is generally comprised of a high voltage (HV) DC power supply 105, an energy storage circuit 107, a pulse power switch 110 and a pulse compressor 120, the pulse compressor 120 shown in detail in FIGS. 2 and 3.

Power supply 105 provides a source of high voltage, typically in the range of 10 to 100 kV. Energy storage circuit 107 stores the high voltage. In a preferred embodiment, energy storage circuit 107 is comprised of at least one energy storage element (e.g., an energy storage capacitor) that is charged by power supply 105. Energy storage circuit 107 may also include one or more inductors.

Switch 110 is connected with energy storage circuit 107, and is operable between an ON condition and an OFF condition. In the ON condition of switch 110, the charge stored in energy storage circuit 107 is applied to pulse compressor 120. The charge stored in energy storage may decay exponentially. In the OFF condition of switch 110, no charge is applied to pulse compressor 120.

As indicated above, operation of switch 110 is controlled by control unit 40. In a preferred embodiment, switch 110 takes the form of a gas-discharge or a semiconductor switch. Gas discharge switches include a hydrogen thyratron or a gas spark gap switch (e.g., triggered spark gap), as well known to those skilled in the art. Semiconductor switches include, but are not limited to, a semiconductor open switch (SOS) and a thyristor. The pulse rate (i.e., pulse frequency) is preferably in the range of 1–10,000 Hz, and more preferably in the range of 1–1,000 Hz. The duration of each pulse is preferably in the range of 20–1,000 $\mu$sec, and more preferably in the range of 50–200 $\mu$sec.

A hydrogen thyratron is a high peak power electric switch that uses hydrogen gas as a switching medium. The switching action is achieved by a transfer from the insulating properties of neutral gas to the conducting properties of ionized gas. Applying the basic principles of gas discharge physics, the hydrogen thyratron is designed to withstand a high voltage in the OFF state, to trigger at a precisely defined time, to pass high peak current pulses in the ON state and to recover rapidly to the OFF state to allow high repetition rate operation. Voltages typically range from 5 kV to 200 kV, with peak current generally in the range of 100 A to 100 kA.

Figure 2:
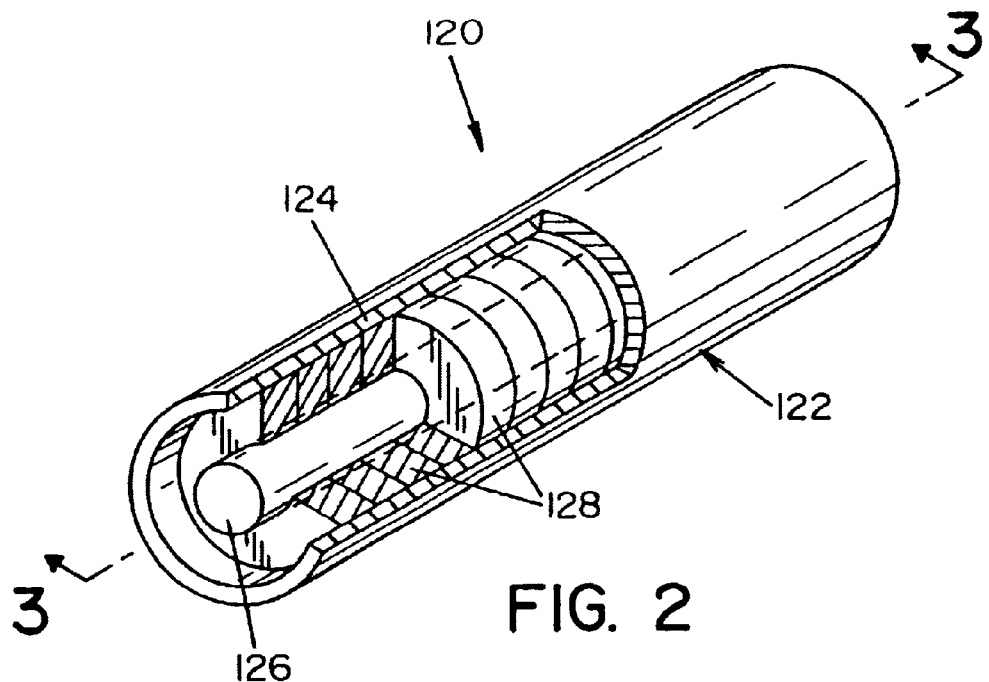
FIG. 2 is a partially sectioned, perspective view of a pulse compressor, according to one aspect of the present invention.
Figure 3:
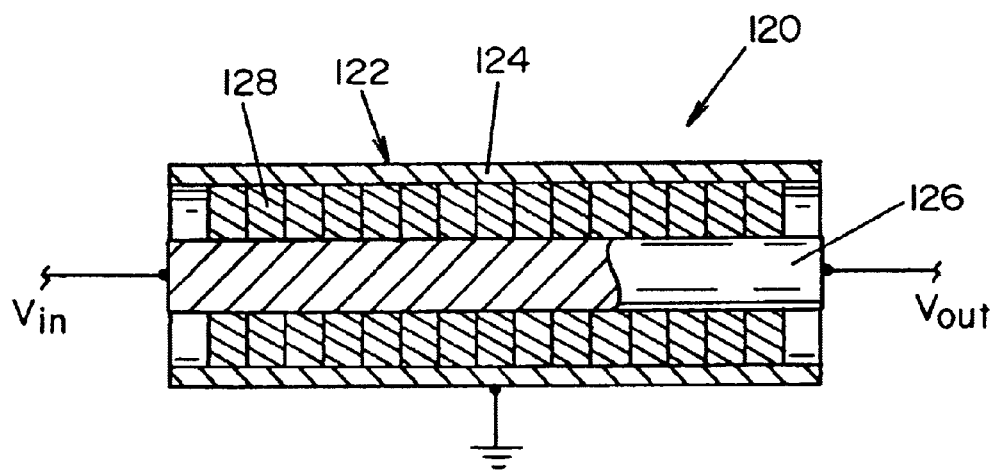
FIG. 3 is a cross-sectional view of the pulse compressor taken along lines 3—3 of FIG. 2.

Referring now to FIGS. 2 and 3, pulse compressor 120 is preferably comprised of a coaxial arrangement 122, including an outer conductor 124, an inner conductor 126, and a magnetic material 128 (preferably a ferrimagnetic material) disposed between outer conductor 124 and inner conductor 126. Outer conductor 124 is preferably cylindrical. In a preferred embodiment, magnetic material 128 takes the form of a plurality of rings. Alternatively, magnetic material 128 may take the form of one or more cylinders. It should be understood that the geometry of inner conductor 126 shown in FIGS. 2 and 3 is solely for the purpose of illustrating a preferred embodiment of the present invention. In this regard, inner conductor 126 may have alternative geometries, including, but not limited to, a generally planar elongated plate. Inner and outer conductors 126, 124 are preferably made of a metal having high electrical conductivity, such as copper. Ferrimagnetic material 128 is preferably made of a ferrite (i.e., an electrically high-resistance magnetic material consisting principally of ferric oxide and one or more other metals). The typical formula for a ferrite is $MO.Fe_2O_3$, where M is a divalent cation, often Zn, Cd, Fe, Cu, Co, or Mg (e.g., $Zn.Fe_2O_3$).

The voltage applied by switch 110 is received at one end of inner conductor 126 of coaxial arrangement 122, as the input voltage ($V_m$) of pulse compressor 120. As indicated above, switch 110 applies the output voltage of power supply 105 in an ON condition, and applies no voltage in an OFF condition. Accordingly, the alternating operation of switch 110 between the ON and OFF conditions produces high voltage pulses.

Output voltage ($V_{out}$) of pulse compressor 120 is output at the opposite end of inner conductor 126. Outer conductor 124 is connected to ground. Pulse compressor 120 functions to shorten the rise time of the input pulse associated with $V_m$ (see FIG. 4A), that is generated by operation of switch 110. The rise time is shortened by $\Delta t$, to produce an output pulse as shown in FIG. 4B. It should be appreciated that $\Delta t$ is typically 1 to 70 nsecs. Operation of pulse compressor 120 will be described in further detail below.

Figure 5:
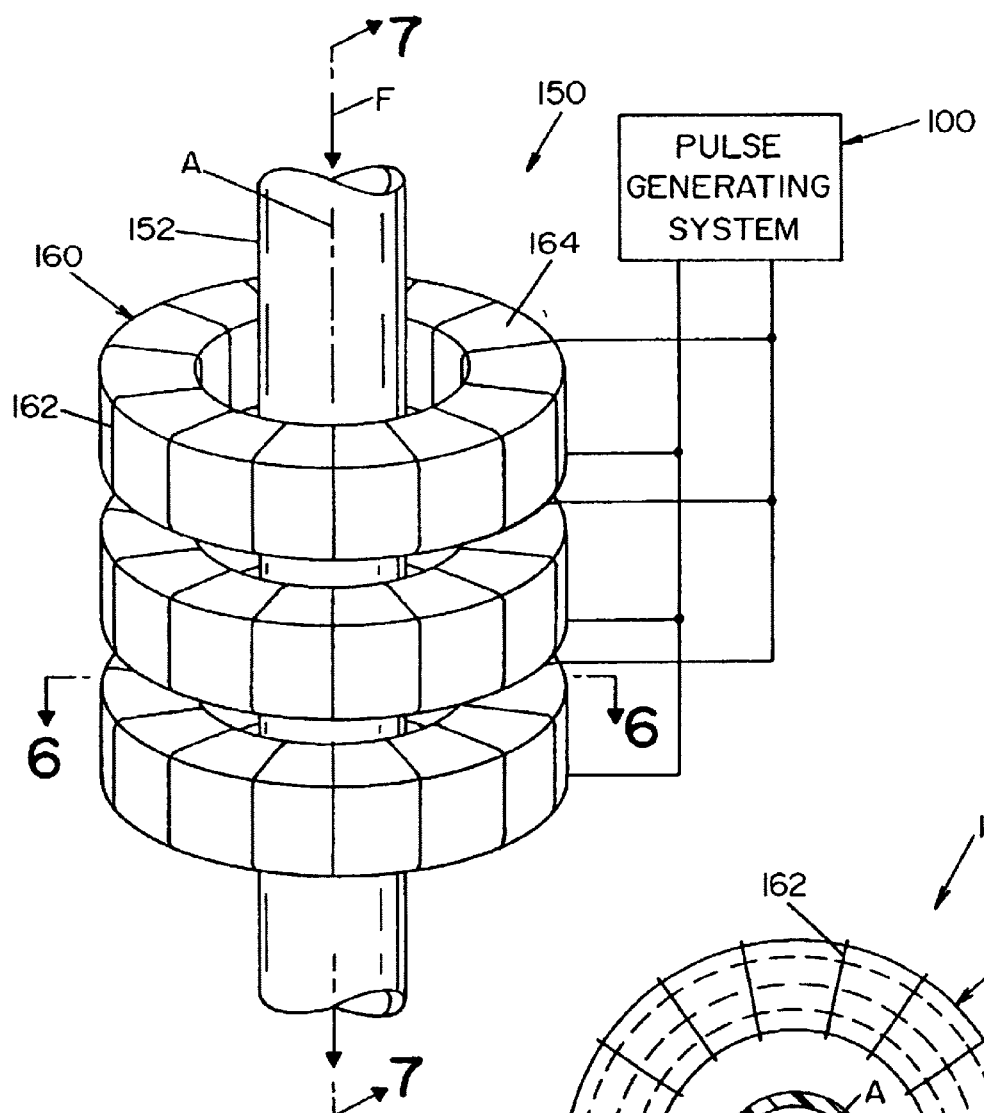
FIG. 5 is a perspective view of a treatment assembly, according to a preferred embodiment of the present invention.
Figure 6:
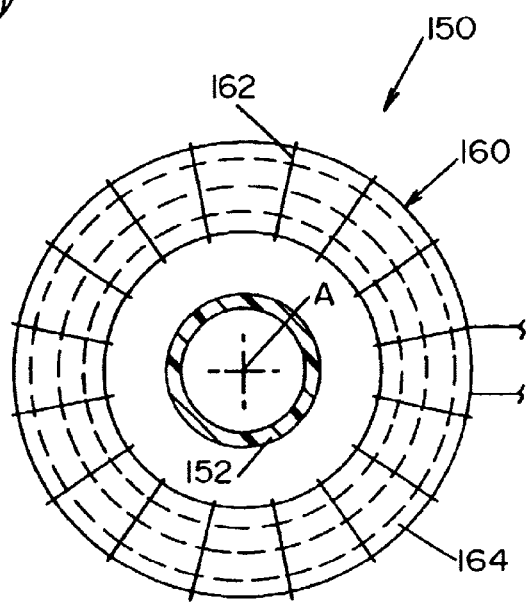
FIG. 6 is a cross-sectional view of the treatment assembly, taken along lines 6—6 of FIG. 5.
Figure 7:
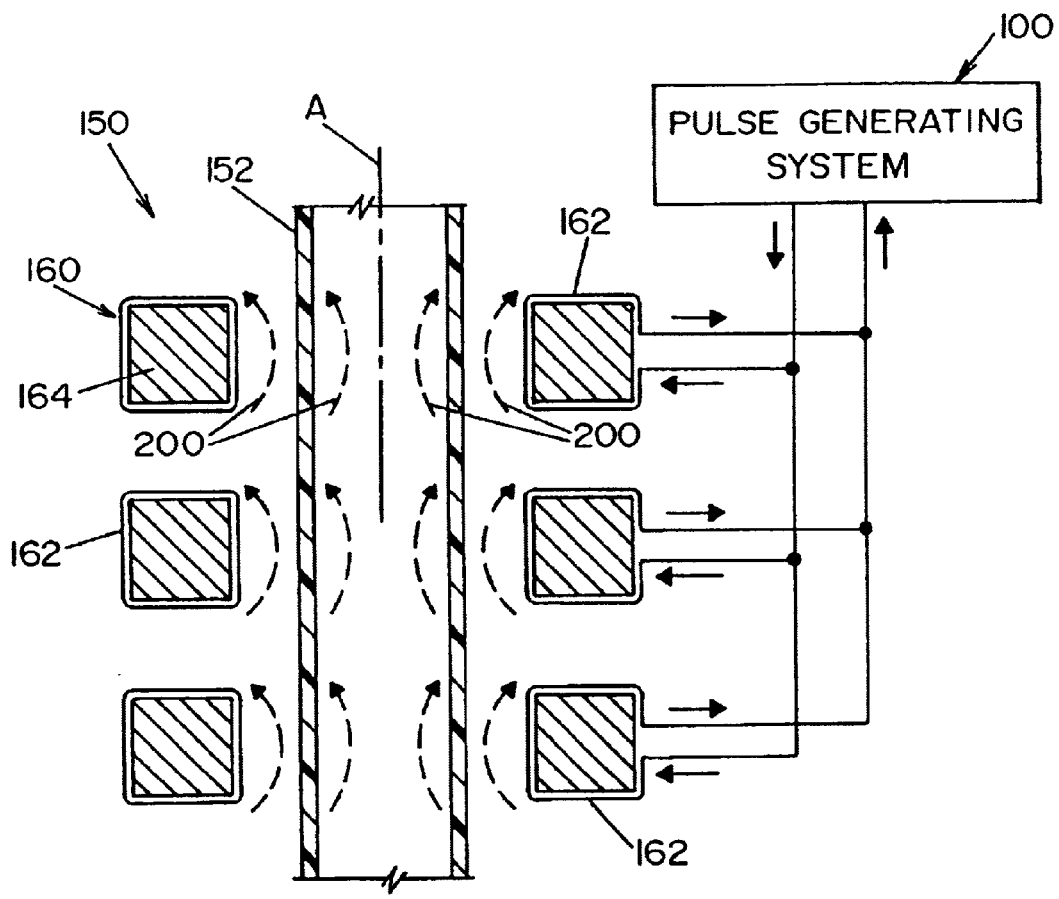
FIG. 7 is a cross-sectional view of the treatment assembly, taken along lines 7—7 of FIG. 6, illustrating electric and magnetic fields produced in the treatment assembly.

Referring now to FIGS. 5–7, treatment assembly 150 is generally comprised of flow tube 152 surrounded by a plurality of inductors 160. Flow tube 152 defines a passageway for the fluid medium. As best seen in FIGS. 6 and 7, flow tube 152 and inductors 160 are coaxially aligned along an axis A. Flow tube 152 is preferably formed of a dielectric material suitable for contact with liquid foods (i.e., will not contaminate or render harmful a liquid food). By way of example, and not limitation, flow tube 152 may be formed of glass or Teflon™. It should be appreciated that the dimensions of flow tube 152 are not limited by the requirements of a maximum gap size between a pair of electrodes, as in the case of prior art PEFs.

In a preferred embodiment, inductors 160 are comprised of wire coils 162, wound on toroidal cores 164. Cores 164 may be formed of a suitable material, including, but not limited to permalloy (i.e., a high-permeability alloy of iron and nickel), ferrite (i.e., an electrically high-resistance magnetic material consisting principally of ferric oxide and one or more other metals), and amorphous iron (i.e., a noncrystalline iron).

Each core 164 multiplies the inductance of associated wire coils 162 by the permeability of the core material. As well known to those skilled in the art, "inductance" refers to a measure of a coil's ability to store energy in the form of a magnetic field. Permeability ($\mu$) provides a measure of the comparative ease with which magnetic flux can be set up in a material. A magnetic material with a high relative permeability (i.e., easily magnetized) concentrates magnetic flux and produces a large value of magnetic flux density $\beta$ for a magnetic field B.

Considering the permeability to be constant for the material forming cores 164, then $$L=N\Phi/I,$$

where L is the inductance (henrys), N is the total number of turns in the coil, and I is the current (amps). Inductance is related directly to the energy represented by the surrounding magnetic field by the following mathematical relationship:

$$L=(2)(W)/I^2,$$

where W is the field energy in Joules. Therefore, $W=\frac{1}{2}LI^2$.

Wire coils 162 are located around the periphery of flow tube 152, and are connected with the output of pulse compressor 120 to receive $V_{out}$ (see FIG. 4B) of pulse compressor 100. Flow tube 152 provides a passageway for the fluid medium to pass through a pulsed electric field associated with inductors 160, as will be described in detail below. Flow tube 152 physically isolates the electrical components of treatment assembly 150 from the fluid medium flowing therethrough.

A cooling unit (not shown) may be provided along the path between treatment assembly 150 and treated product storage container 24. The cooling unit may take the form of cooling coils.

The following is an overview of the operation of PEF processing system 10. Pump 30 is operable to pump fluid medium out of initial product storage container 22, and through flow tube 152 of treatment assembly 150, where it passes through an electric field. After sufficient exposure to the pulsed electric field, the treated fluid medium flows into treated product storage container 24. As indicated above, the treated fluid medium may pass through a cooling unit (not shown) after exiting treatment assembly 150.

Figure 4A:
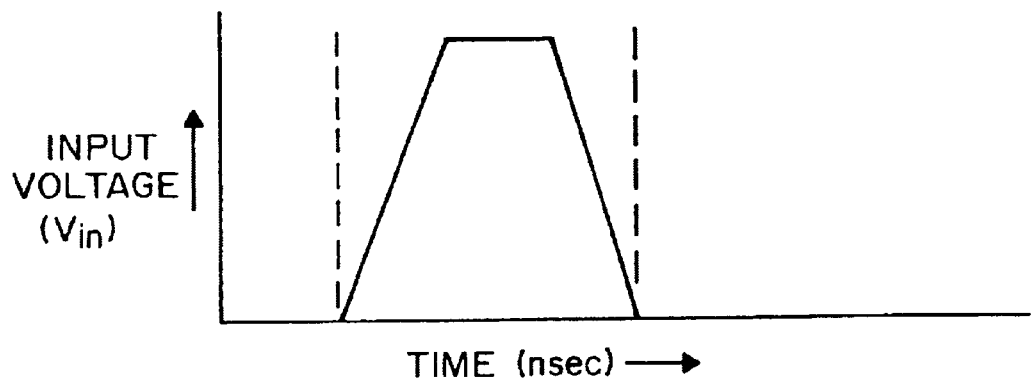
FIG. 4A is a waveform diagram illustrating an input pulse to the pulse compressor of FIGS. 2 and 3, as produced by operation of a switch.
Figure 4B:
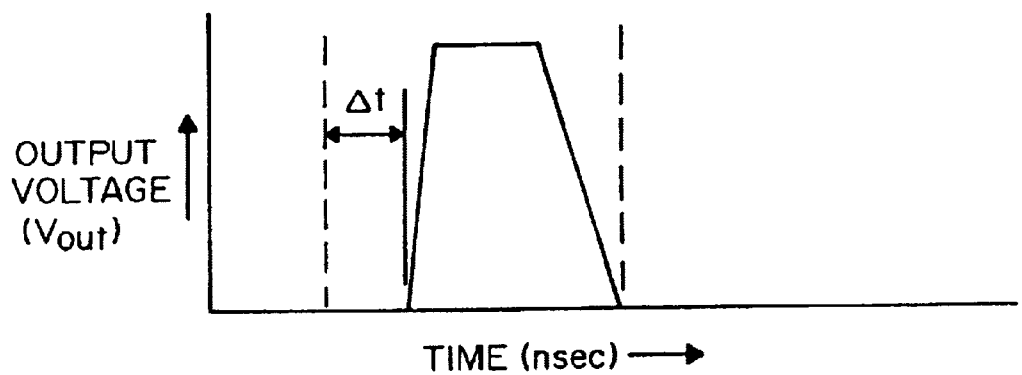
FIG. 4B is a waveform diagram illustrating an output pulse of the pulse compressor of FIGS. 2 and 3.

Turning now to a detailed description of the operation of PEF processing system 10, control unit 40 operates switch 110 to form a continuous series of high voltage pulses, as shown in FIG. 4A. Each high voltage pulse is processed by pulse compressor 120 to produce a compressed high voltage pulse. In this regard, pulse compressor 120 reduces the rise time of each high voltage pulse by $\Delta t$ (see FIG. 4B). Pulse compressor 120 utilizes the effect of non-linear dissipation of electromagnetic waves in magnetic material 128 (also known as the "Arkediev Effect") to decrease the rise time of each high voltage pulse. The rise time of the high voltage pulse is reduced from about 50 to 75 nsec to about 1 to 10 nsec. Accordingly, the slope of the rising voltage pulse waveform is significantly increased. It should be appreciated that pulse compressor 120 operates to remove low frequency signals from the pulse waveform.

The compressed high voltage pulses produced by pulse compressor 120 are applied to wire coils 162 of treatment assembly 150. The compressed high voltage pulses produce a pulsed electric field. The process for producing the pulsed electric field in accordance with a preferred embodiment of the present invention, will now be described in detail.

As electric current associated with the compressed high voltage pulses passes through wire coils 162 wound on a core 164, a magnetic field B is induced. Specifically, the current in the coils produce a magneto-motive force (mmf) according to $F_m=(I)(N)$, wherein $F_m$ is the magneto-motive force in ampere-turns, I is the current in amps, and N is the total number of turns in the coils.

The magneto-motive force $F_m$ produces a magnetic field B, according to $B=F_m/I^e$, where B is the magnetic field in ampere-turns per meter, and $I^e$ is the effective magnetic path length. The effective magnetic path length is a measure of the distance which magnetic flux lines travel in making a complete circuit.

The magnetic field B produces magnetic flux density $\beta$ according to $\beta=(\mu)(B)$ tesla, where $\mu$ is the permeability. The total magnetic flux $\Phi$ is calculated by summing the magnetic flux density $\beta$ over the cross-sectional area of the core, according to $\Phi=(\mu)(A_e)$ webers, where $A_e$ is the effective area of the core.

Changes to the magnetic flux $\Phi$ (i.e., by pulsing the voltage applied to wire coils 162) produce an induced or "instantaneous" voltage ϵ, known as an emf or electromotive force. In this regard, $\epsilon = N (d\Phi/dt)$ in volts or Joules/coulomb, where N is the number of turns in a conducting loop through which the magnetic flux ($\Phi$) is changing. This mathematical relationship is well known to those skilled in the art as Faraday's law. Likewise, whenever magnetic flux ($\Phi$) through a given area or loop changes with time, an electric field is induced around the perimeter of that area or loop that opposes the change in magnetic flux ($\Phi$) that produced it (Lenz's Law).

The fast rise time (i.e., large slope) of the output voltage waveform shown in FIG. 4B will result in a rapidly changing magnetic flux $\Phi$, as the output voltage quickly changes. The rapidly changing magnetic flux $\Phi$ will induce a large emf ϵ and pulsed electric field. During periods when the output voltage is not changing, the magnetic flux ($\Phi$) is not changing, and thus no induced voltage or electric field is produced. Consequently, a series of high voltage pulses having fast rise times (i.e., large slopes), and a high pulse rate (i.e., frequency), will result in a pulsed electric field.

As can be observed from FIG. 7, the electric lines 200 of the induced pulsed electric field are in the same direction. Thus, the lines of force aid each other, making the electric field in the center of the toroid stronger. The fluid medium flowing through tube 152 is exposed to the induced pulsed electric field, as the fluid medium flows through tube 152. Exposure to the pulsed electric field results in treatment of the fluid medium.

The pulsed electric field induces an electric potential difference across cell membranes, referred to as transmembrane potential. Permeability of a cell membrane increases when the transmembrane potential reaches a critical value. The increase in permeability results from "electroporation" or pore formation in the cell membrane. Electroporation refers to the electrically induced reversible permeabilization of cells. Exposure of cells to electric fields induces electroporation, resulting in the inactivation of microorganisms.

As reported by Qin et al. in *Critical Reviews in Food Science and Nutrition*, CRC Press, Inc. (1996), in an article entitled "*Nonthermal Pasteurization of Liquid Foods Using High-Intensity Pulsed Electric Fields*," several theories have been proposed to explain the mechanism of electroporation and microbial inactivation. In this regard, the electric breakdown of biological membranes has been explored extensively based on model systems such as liposomes, planar bilayers, and phospholipid vesicles, because the lipid bilayer membranes exhibit properties similar to the cell membranes. The breakdown of lipid bilayers and biological cell membranes is based on (1) threshold transmembrane potential, (2) compression of the bilayer or cell membrane, (3) viscoelastic properties of cell membranes, (4) fluid mosaic arrangement of lipids and proteins in the cell membrane, (5) structural defects in the membranes, and (6) colloidal osmotic swelling. When exposed to a strong electric field, the bilayers of membranous phospholipid vesicles are polarized because of the movement of ions along the electric field lines. Because the lipid bilayer is a poor conducting medium, the ions accumulate at the surface of the bilayer and generate a transmembrane potential. When the induced transmembrane potential is greater than the natural potential of the cell (~1 V), rupture takes place. The rupture leads to the formation of pores in the membrane.

In summary, it is believed that under the influence of the pulsed electric field, charged particles in the fluid medium produce what may be termed as a sequence of "shock waves" that destroy cell membranes, thus resulting in electroporation and microbial inactivation of the cell.

As will be appreciated by one skilled in the art, the strength of the electric field within the fluid medium can be determined by Maxwell's equations.

The present invention provides a method and apparatus for the treatment of a fluid medium to inactivate biocontamination, including, but not limited to, bacteria, microbes, viruses and prions, using a pulsed electric field. It is believed that the pulsed electric field of the present invention affects charged particles within the fluid resulting essentially in a "shock wave" that breaks down microbial cell structures in the fluid. The present invention does not require the use of electrodes, and effectively treats a fluid medium using lower voltages than prior art systems. Moreover, the fluid medium is isolated from electrical components of the system, and can be passed through the electric field at a higher throughput than in prior art systems. It is contemplated that the present invention finds usefulness in the fields of sterilization, pasteurization, treatment of human consumable liquids (e.g., water, juice, soda, tea, coffee, and the like), and gas depollution and de-contamination.

Other modifications and alterations will occur to others upon their reading and understanding of the specification. It is intended that all such modifications and alterations be included insofar as they come within the scope of the invention as claimed or the equivalents thereof.

Having described the invention, the following is claimed:

1. An apparatus for exposing a fluid medium to a pulsed electric field, comprising:
   an energy storage circuit chargeable by a high voltage source;
   switch means connected with the energy storage circuit, said switch means operable to form high voltage pulses;
   a pulse compressing means for receiving the high voltage pulses and reducing a rise time for each of said high voltage pulses to produce a series of compressed high voltage pulses having a decreased rise front; and
   a treatment assembly for receiving the fluid medium, said assembly comprising:
      a dielectric flow tube providing a passageway for the fluid medium to travel through the treatment assembly, and
      inductance means for receiving the series of compressed high voltage pulses, said inductance means producing a changing magnetic field in response to a change in voltage, which in turn induces an electric field, said electric field being pulsed in response to the compressed high voltage pulses, wherein said fluid medium passes through said pulsed electric field.

2. An apparatus as defined by claim 1, wherein said pulse compressing means includes:
   an outer conductor connected to ground;
   an inner conductor connected with said switch means; and
   a magnetic material located between the inner and outer conductors.

3. An apparatus as defined by claim 2, wherein said magnetic material is a ferrimagnetic material.

4. An apparatus as defined by claim 1, wherein said inductance means includes:
   one or more coils of wire, wherein said coils of wire surround said flow tube.

5. An apparatus as defined by claim 4, wherein said inductance means includes:
   one or more toroids comprised of a material selected from the group consisting of: a permalloy, a ferrite, and amorphous iron, wherein said coils of wire are wound on said toroids.

6. An apparatus as defined by claim 1, wherein said flow tube physically isolates the fluid medium from electrical components of said treatment assembly.

7. An apparatus as defined by claim 1, wherein said energy storage circuit includes at least one energy storage capacitor.

8. A method for exposing a fluid medium to a pulsed electric field, comprising:

switching an energy storage element to form high voltage pulses;

compressing the high voltage pulses to reduce a rise time of each pulse, thereby producing compressed high voltage pulses;

exciting inductance means with the compressed high voltage pulses, wherein said compressed high voltage pulses produce a changing magnetic field, which in turn induces an electric field;

producing a series of electric field pulses in response to the high voltage pulses; and exposing the fluid medium to the pulsed electric field.

9. A method as defined by claim 8, wherein said step of compressing said high voltage pulses includes passing said high voltage pulses through a co-axial conducting means having an outer conductor connected to ground, an inner conductor, and a magnetic material located therebetween.

10. A method as defined by claim 8, wherein said inductance means includes one or more coils of wire, said coils of wire surrounding a flow tube through which the fluid medium passes.

11. A method as defined by claim 10, wherein said coils of wire are wound on one or more toroids, said toroids comprised of a material selected from the group consisting of: a permalloy, a ferrite, and amorphous iron.

12. An apparatus for producing compressed pulses, comprising:

an outer conductor connected to ground;

an inner conductor connected with a switchable voltage source to receive one or more pulses of voltage having a first rise time; and a magnetic material located between the inner and outer conductors.

13. An apparatus as defined by claim 12, wherein said magnetic material is a ferrimagnetic material.

14. An apparatus as defined by claim 13, wherein said ferrimagnetic material is a ferrite.

15. An apparatus as defined by claim 14, wherein said ferrite is $MO.Fe_2O_3$, where M is a divalent cation selected from the group consisting of: Zn, Cd, Fe, Cu, Co, and Mg.

16. An apparatus as defined by claim 12, wherein said magnetic material is configured as a plurality of rings.

17. An apparatus as defined by claim 12, wherein said first rise time is reduced by 1 nsec to 70 nsec to produce a compressed output pulse.

18. An apparatus for exposing a fluid medium to a pulsed electric field, comprising:

a source of high voltage pulses; and a treatment assembly including:

inductance means for receiving the high voltage pulses and inducing a pulsed electric field in response to the high voltage pulses, and a passageway physically isolated from the inductance means, to pass the fluid medium through the pulsed electric field.

19. An apparatus as defined by claim 18, wherein said source of high voltage pulses includes a pulse compression means for generating high voltage pulses having a relatively short rise time.

20. An apparatus as defined by claim 19, wherein said pulse compression means includes:

an outer conductor connected to ground;

an inner conductor; and a magnetic material located between the inner and outer conductors.

21. An apparatus as defined by claim 18, wherein said inductance means includes:

one or more coils of wire, wherein said coils of wire surround said passageway.

22. An apparatus as defined by claim 21, wherein said inductance means further includes:

one or more toroids comprised of a material selected from the group consisting of: a permalloy, a ferrite, and amorphous iron, wherein said coils of wire are wound on said toroids.

23. An apparatus as defined by claim 18, wherein said passageway is defined by a flow tube.

24. An apparatus as defined by claim 23, wherein said flow tube is made of a dielectric material.

25. An apparatus as defined by claim 18, wherein the fluid medium is a liquid consumable by humans.

26. An apparatus as defined by claim 25, wherein the liquid consumable by humans is selected from the group consisting of: water, juice, soda, tea and coffee.

27. A method for exposing a fluid medium to a pulsed electric field, comprising:

generating a series of high voltage pulses; and exciting inductance means with the series of high voltage pulses, wherein a pulsed electric field is induced in response to the high voltage pulses;

exposing the fluid medium to the pulsed electric field, wherein the fluid medium is physically isolated from the inductance means.

28. A method as defined by claim 27, wherein said method further includes:

compressing said series of high voltage pulses prior to excitation of the inductance means.

29. A method as defined by claim 28, wherein said step of compressing said high voltage pulses includes passing said high voltage pulses through a co-axial conducting means having an outer conductor connected to ground, an inner conductor, and a magnetic material located therebetween.

30. A method as defined by claim 27, wherein said inductance means includes one or more coils of wire, said coils of wire surrounding a flow tube through which the fluid medium passes.

31. A method as defined by claim 30, wherein said coils of wire are wound on one or more toroids, said toroids comprised of a material selected from the group consisting of: a permalloy, a ferrite, and amorphous iron.

32. A method as defined by claim 27, wherein the fluid medium is a liquid consumable by humans.

33. A method as defined by claim 32, wherein the liquid consumable by humans is selected from the group consisting of: water, juice, soda, tea and coffee.

* * * * *